United States Patent [19]
Cude

[11] Patent Number: 5,960,837
[45] Date of Patent: Oct. 5, 1999

[54] SUCTION CANISTER HAVING MOLDED INTERLOCKING LID

[75] Inventor: J. Michael Cude, Woodburn, Ky.

[73] Assignee: DeRoyal Industries, Inc., Powell, Tenn.

[21] Appl. No.: 08/985,929

[22] Filed: Dec. 5, 1997

[51] Int. Cl.[6] .................................................. A61M 1/00
[52] U.S. Cl. .............................. 141/65; 141/59; 137/205; 604/319; 220/786
[58] Field of Search .................................. 141/59, 65, 67; 137/205; 604/319–321; 220/784–786

[56] References Cited

U.S. PATENT DOCUMENTS

| | | | |
|---|---|---|---|
| 2,977,019 | 3/1961 | Henchert | 220/784 |
| 3,782,414 | 1/1974 | Holbrook | 604/319 |
| 3,965,902 | 6/1976 | Reilly et al. | 141/59 |
| 4,430,084 | 2/1984 | Deaton | 141/67 |
| 5,185,007 | 2/1993 | Middaugh et al. | 604/320 |
| 5,254,080 | 10/1993 | Lindsay | 604/319 |
| 5,381,918 | 1/1995 | Dahl | 220/784 |
| 5,538,154 | 7/1996 | Von Holdt | 220/784 |

OTHER PUBLICATIONS

Product Brochure: Receptal, 1987, Abbott Laboratories, Hospital Products Division, North Chicago, IL 60064: 4 pages.
Product Brochure: New from EZE–VAC, 1991, Abbott Laboratories, Hospital Products Division, North Chicago, IL 60064, 4 pages.
Product Brochure: Medi–Vac CRD Suction System, 1995, Baxter Healthcare Corporation, McGaw Park, IL 60085, 2 pages.
Product Brochure: Bemis System II, 1994, Bemis Healthcare, Sheboygan Falls, WI 53085, 2 pages.
Product Brochure: Bemis System III, 1994, Bemis Healthcare, Sheboygan Falls, WI 53085, 2 pages.
Product Brochure: Bemis 800 cc System III, 1994, Bemis Healthcare, Sheboygan Fall, WI 53085, 2 pages.

*Primary Examiner*—J. Casimer Jacyna
*Attorney, Agent, or Firm*—Pitts & Brittian, P.C.

[57] ABSTRACT

A suction canister particularly suitable for the collection of waste fluids from a medical patient including an open-top receptacle and a lid adapted to close the open-top of the receptacle. The receptacle and lid are each readily and inexpensively moldable from plastic materials employing existing molding techniques and facilities. The outer rim of the open top of the receptacle and the peripheral margin of the lid are adapted to provide engagement of the lid with the rim of the receptacle, such engagement providing a positive and readily identifiable limit of the extent of the engagement that provides a certain sealing of the id with the receptacle rim, and resulting in an interlocking of the lid with the receptacle as prevents removal of the lid from the receptacle other than by destructive force applied to the lid and/or receptacle.

5 Claims, 3 Drawing Sheets

SUCTION CANISTER HAVING MOLDED INTERLOCKING LID

BACKGROUND OF INVENTION

The present invention relates to suction canisters of the type commonly used for collection of waste fluids from a medical patient, such as collection of the fluid drainage associated with a surgical site. These suction canisters include an open-top receptacle for the waste fluids and a lid which closes the open-top of the receptacle. The receptacle and the lid most commonly are fabricated from plastic materials by molding techniques. In plastic molding, the receptacle and the lid can not be formed as a complete unit due to physical limitations relating to the molding process. Therefore, the receptacle and lid are manufactured as separate units and must be assembled prior to use.

The fluids normally collected in a suction canister commonly contain infectious matter. Pursuant to acceptable operating procedures for medical facilities, the collected fluids are to be disposed of in a manner which destroys the infectivity potential of the fluids and/or canister, and which guards against inadvertent contact between the fluids and a health care worker. It is common therefore either to provide an inner liner within the canister which captures the fluids and which is removable for disposal, or to cap off the entry and exit openings to the canister and dispose of the fluids and canister simultaneously. The procedure employing a liner within the canister is intended to permit reuse of the canister and its lid, and therefore suffers from the problem of potential exposure to a health care worker when the lid is removed and the liner is closed and retrieved from the canister. In known prior art canister and lid combinations, the lid is secured to the open top end of the canister as by threads or by friction fit between the lid and the canister. These methods of attachment are intended to ensure a vacuum seal between the lid and the open end of the canister, hence each technique requires the health care worker to exert sufficient force to the lid to ensure that it seals properly with the canister. Further, each such technique provides a measure of adjustability with respect to the extent to which the lid can be applied to the canister, thereby requiring the health care worker to judge when the lid is sufficiently sealed to the canister. Through the natural tendency of a health care worker to want to ensure a good seal between the lid and the canister, the worker may tend to apply excessive force to the lid. This excessive force causes the lid to be inordinately difficult to remove when the canister is filled with liquids, so that removal of the lid under these circumstances subjects the worker to potential inadvertent exposure to the liquids if the force applied to remove the lid causes the lid to open in an uncontrolled manner. Both these prior lid attachment techniques permit removal of the lid after the canister contains fluids and therefore provide little or no assurance that the canister will not be opened, either purposefully or inadvertently, between its point of use and its point of final disposal.

It is therefore an object of the present invention to provide a suction canister which includes a receptacle and lid which can be readily assembled at the point of use, wherein the sealing of the lid to the open-top end of the receptacle is positive, and wherein the lid, after being assembled in sealing relationship to the receptacle, is essentially non removable by non-destructive force applied to the lid.

Other objects and advantages of the present invention will be recognized from the description contained herein including the claims and the drawings.

SUMMARY OF INVENTION

In accordance with the present invention there is provided a suction canister particularly suitable for the collection of waste fluids from a medical patient including an open-top receptacle and a lid adapted to close the open-top of the receptacle. The receptacle and lid are each readily and inexpensively moldable from plastic materials employing existing molding techniques and facilities. The outer rim of the open top of the receptacle and the peripheral margin of the lid are adapted to provide engagement of the lid with the rim of the receptacle, such engagement providing a positive and readily identifiable limit of the extent of the engagement that provides a certain sealing of the lid with the receptacle rim, and resulting in an interlocking of the lid with the receptacle as prevents removal of the lid from the receptacle other than by destructive force applied to the lid and/or receptacle.

In accordance with one aspect of the present invention, the interlocking of the lid with the receptacle rim is accomplished by means of a plurality of ramped ledges provided in spaced apart relationship to one another on the interior surface of a peripheral skirt of the lid that resiliently yields to allow the peripheral shoulder on the receptacle rim to pass over the ramped ledges in the course of applying the lid to the receptacle and which resiliently rebounds after passing over the receptacle rim to positively engage the rim to interlock the lid with the rim. In a preferred embodiment, the side wall of the receptacle, at the top end of the receptacle, is partially folded outwardly of the receptacle and back upon itself to define a continuous annular top end of the receptacle and a continuous integral annular skirt that depends from the top end of the receptacle and lies along, but preferably spaced apart from, the exterior surface of the wall of the receptacle. This annular skirt is substantially inflexible. Once a ramped ledge passes over the lower edge of the skirt, the ledge is engaged with the lower edge of the skirt and the resiliency of the peripheral skirt of the lid applies to the annular skirt of the receptacle a force which urges the top end of the receptacle into positive sealing engagement with the lid. To this end, the lid includes an annular flange that depends from the inner surface of the lid at a location spaced inwardly from the peripheral skirt to define an annular trough suitable for receipt of the top edge of the receptacle therein such that there is developed sealing engagement of the top edge of the receptacle with the trough when the top end of the receptacle is urged into physical engagement with the wall of the trough. It is this urging of engagement between the top end of the receptacle and the wall of the trough that is provided by the force exerted by the resilient peripheral skirt of the lid once the ledges on the lid skirt engage the lower edge of the annular skirt of the receptacle. Release of the lid from the rim requires a destructive force applied to the lid in that release of individual ones of the ledges from engagement with the annular skirt of the receptacle is insufficient to permit removal of the lid. Further, in this respect, the use of physically spaced apart ledges on the lid precludes the peeling away of the lid by deflection of the lid from its normal at rest geometry. In this manner, once the lid is assembled with the receptacle, the entire canister and its contents may be disposed of after use, with little or no exposure of a health care worker to the fluid contents of the canister.

In order to mold a lid having ramped ledges provided on the lid as employed in the present invention, the inventor provides an opening through the thickness of the lid skirt adjacent each ramped ledge. Each opening extends from its accompanying ledge upwardly away from the ledge and terminates in a top wall having a planar surface that defines the top wall of the opening and which is disposed not further laterally outwardly of the lid than the innermost edge of the ledge. Preferably the planar surface of this top wall is oriented substantially perpendicular to the upper surface of the ledge. In any event, this opening in the peripheral skirt of the lid permits the designing of a mold that permits the simultaneous forming of the ramped ledges with the remainder of the lid and provides for removal of the molded product from the mold.

DETAILED DESCRIPTION OF INVENTION

Figure 1:
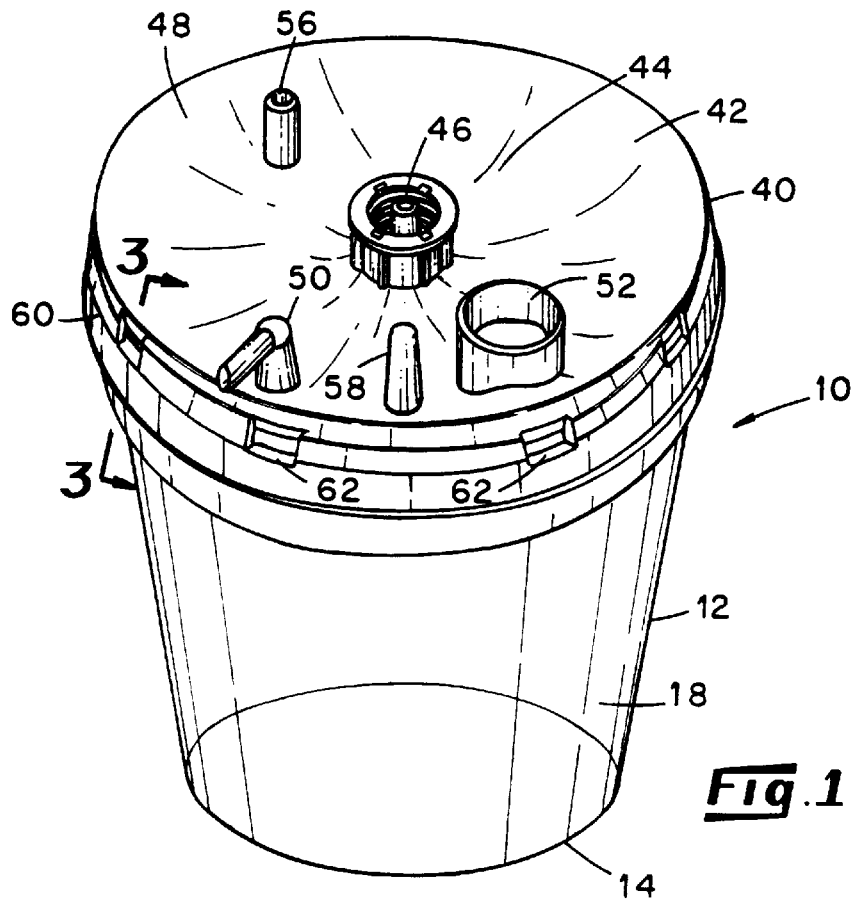
FIG. 1 is a perspective view of one embodiment of a canister embodying various of the features of the present invention.

In the embodiment of the present invention depicted in the several Figures, there is provided a canister 10 suitable for use in the capture of fluids withdrawn from a medical patient, such as from a surgical site on or within the body of the patient. In the present description, it is to be assumed that the canister is disposed uprightly, i.e. having its centerline 11 oriented vertically, unless stated otherwise, and all directions recited are to be referenced to this orientation of the canister. The canister, referred to at times as a suction canister, includes a tapered, generally cylindrical receptacle 12 having a closed bottom end 14, and open top end 16 and wall means 18 connecting the bottom and top ends to define an open-top receptacle. With specific reference to FIGS. 1, 2 and 3, the wall means 18 of the receptacle is folded back over upon itself, in a direction outwardly and downwardly of the receptacle, to define an annular skirt 20 whose innermost wall 22 overlies the uppermost portion 24 of the top portion 26 of the wall means 18, but which is spaced apart therefrom. Preferably, this annular skirt, when viewed in cross-section, defines an angle "A" with respect to the vertical, of about 20 degrees. The folding over of the top edge of the wall means 18 further defines a planar rim 32 on the top end of the wall means. The lower edge 28 of the annular skirt defines a horizontally oriented surface 30 (when the receptacle is disposed uprightly, i.e., vertically). In a preferred embodiment, the receptacle is molded from a plastic, such as a polystyrene plastic which provides substantial rigidity for the receptacle and permits the receptacle to be transparent for visual observation of the contents of the receptacle. Other plastics may be employed, but should be chosen to provide rigidity equivalent to that provided by a polystyrene plastic.

A lid 40 is provided for, among other things, closing the open top end 16 of the receptacle. The lid depicted in the several Figures includes a body portion 42 which in the depicted embodiment includes an annular concave body portion 44 oriented concentrically about an upstanding central port 46 that is adapted to be connected to a source of vacuum such as the usual vacuum connection found in medical treatment facilities. Spaced about the perimetral margin 48 of the lid there are also provided, for example, a port 50 for connecting the interior of the receptacle in fluid flow communication to a wound site or the like from which fluids are to be collected, an accessory port 52 for connecting any of several accessory items such as containers of gelling compound in flow communication to the interior of the receptacle, a tandem port 56 for connecting the interior of the receptacle in tandem fluid flow communication with a further receptacle, and a post 58 for use in storage of caps for one or more of the ports. As desired, other ports, tethered caps for closing off one or more of the ports, etc. may be included on the lid, all as well known in the art.

Figure 2:
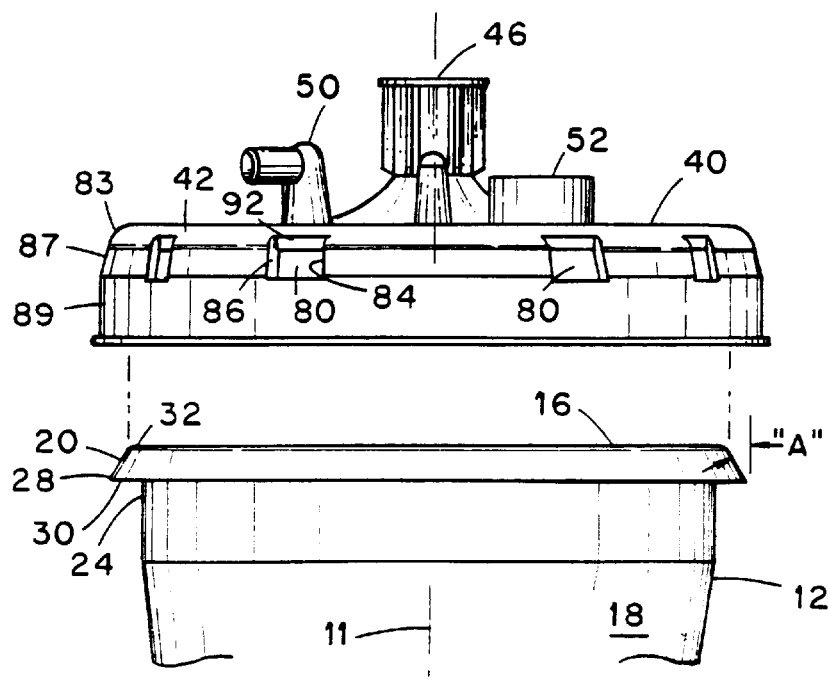
FIG. 2 is a partly exploded side elevational view of the top end of a canister receptacle and lid and depicting the application of the lid onto the open top end of the receptacle.
Figure 3:
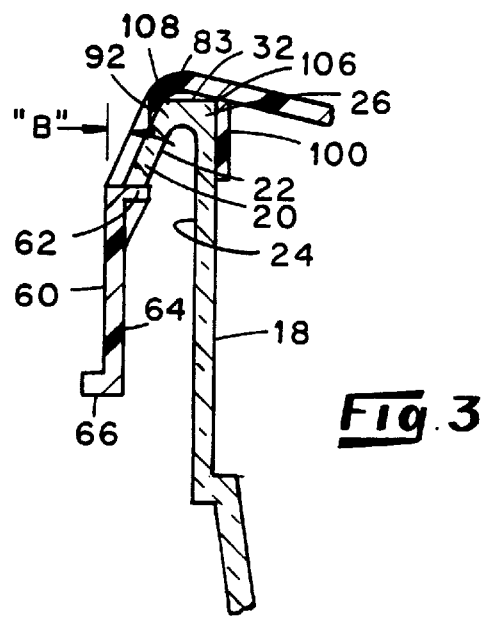
FIG. 3 is a sectional view taken generally along the line 3—3 of FIG. 2 and depicting the interlocking relationship of the lid to the receptacle in accordance with one aspect of the present invention.
Figures 4, 5, 6:
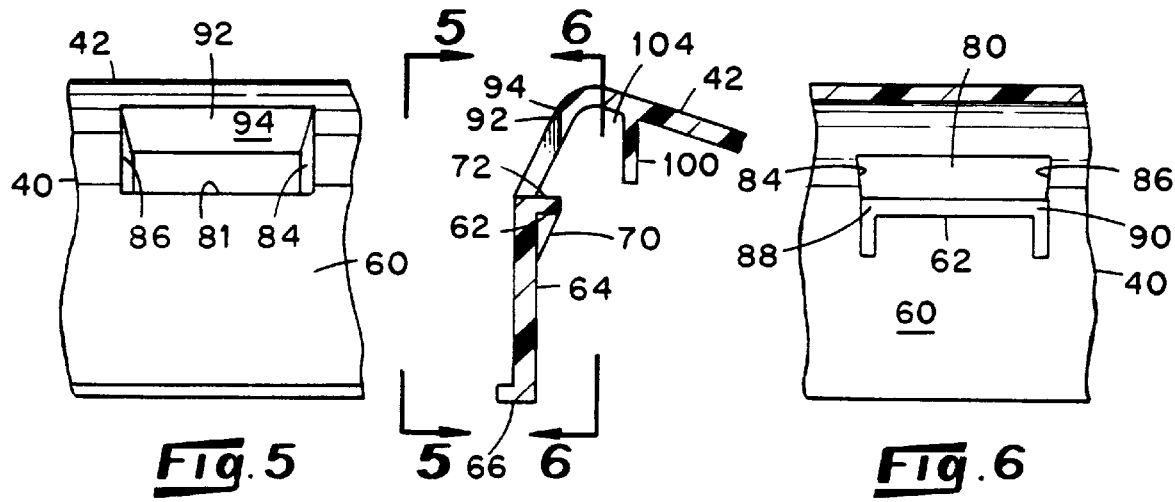
FIG. 4 is a sectional side elevational view of the outer peripheral margin portion of a lid embodying various of the features of the present invention.
FIG. 5 is a side elevational view of the exterior of the lid portion depicted in FIG. 4 and taken generally along line 5—5 of FIG. 4.
FIG. 6 is a side elevational view of the interior of the lid portion depicted in FIG. 4 and taken generally along line 6—6 of FIG. 4.

In the depicted lid 40, the body portion 42 thereof includes an annular perimetral skirt 60 which is integrally formed with the body portion 42 of the lid and depends therefrom to terminate in a circumferential rim 66. In a preferred embodiment, the junction 83 of the body portion of the lid and skirt, when viewed in cross-section as in FIGS. 2 and 3, is radiussed such that the skirt includes an annular portion 87 that projects both downwardly and outwardly from the junction 83, for example at an angle "B" of about 20 degrees with respect to the vertical. In the depicted embodiment, the skirt 60 includes a further integral annular portion 89 which is a continuation of the portion 87. In the depicted embodiment, this skirt is provided with a plurality of integrally molded ledges 62 disposed in spaced apart relationship to one another circumferentially about the inner wall 64 of the skirt 60, for example, about 45 degrees apart. In the preferred embodiment, each ledge 68 projects substantially prependicularly from the skirt 60 to define an upper surface 72 and an outboard edge 70 thereof. Each ledge includes one or more ramps 68 which are inclined in a direction from the inner wall 64 of the skirt 60 toward the outboard edge 70 of their respective ledge, each ramp being disposed on that side of the ledge nearest the rim 66 of the skirt. The lid of the present invention is molded from a plastic material such as high density polyethylene which is chosen to provide, among other things, a degree of resiliency to the skirt 60 of the lid. Accordingly, the skirt 60 of the present lid is amenable to being deformed outwardly from the body 42 of the lid by a distance that is only sufficient to permit the skirt 60 to pass the edge 70 of each ledge 60, and when released will rebound to its original position.

Figure 7:
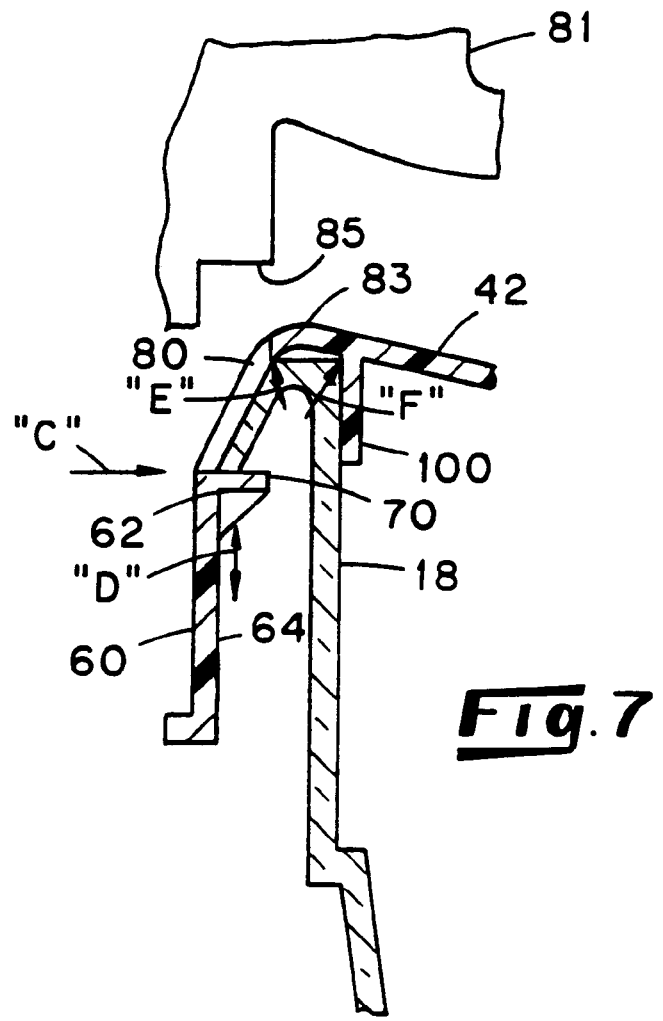
FIG. 7 is a sectional side elevational view of the outer peripheral margin portion of a lid depicting various force vectors associated with the sealing and retention of the lid upon a receptacle, and further depicting a portion of a mold employed in the fabrication of the lid, in accordance with one aspect of the present invention.
Figure 8:
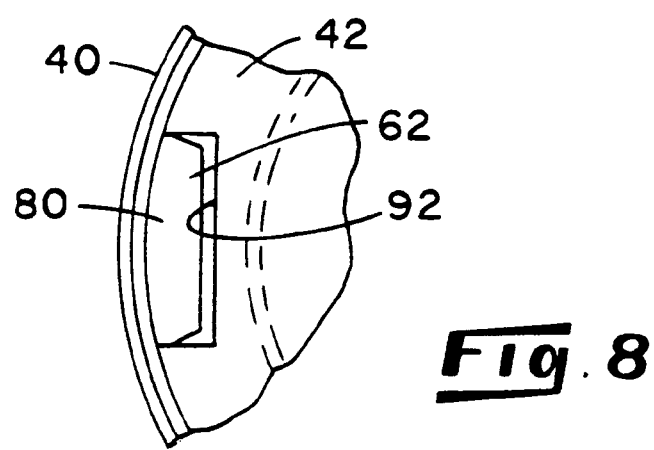
FIG. 8 is a partial top view of a lid and depicting a ledge and its associated opening in accordance with one aspect of the present invention.

In accordance with one aspect of the present invention, each ledge has associated therewith an opening 80 which extends through the thickness of the skirt 60. Referring particularly to FIGS. 3 and 7, this opening is required to enable the molding of a ledge on the inner surface 64 of the skirt and thereafter to extract the molded lid from a mold 81.

To this end, each opening 80 includes a bottom wall 81 which defines a portion of a respective ledge 62, substantially parallel side walls 84 and 86 which extend upwardly from the opposite side ends 88 and 90 of a respective ledge, and an upper wall 92. The width of the opening 80 between its opposite side walls is not less than, and preferably substantially equal to, the length dimension of the ledge 62. The height of the opening is a function of the slope or curvature of the junction 83 between the skirt 60 and the body portion 42 of the lid, but in any event, the upper wall includes a planar surface 94, no portion of which projects laterally outwardly of the lid by a distance greater than the inward limit of the outboard edge 70 of a respective ledge. This configuration of the walls of the opening 80 is important for purposes of designing a mold 81 which includes a shoulder 85 suitable for forming the ledge during molding of the lid, and which will permit the formation of integral ledges projecting from the inner surface of the skirt, and subsequent removal of the molded lid from the mold. As will be seen further hereinafter, this configuration further makes possible the non-removable nature of the interlocking and sealing of the lid to the receptacle.

The lid 40 further includes an annular flange 100 which is integrally formed with, and depends from the inner surface 102, of the body portion 42 of the lid at a location spaced inwardly from the skirt 60 to define an annular trough 104 between the skirt and flange for the receipt therein of the top rim 32 of the receptacle. As best seen in FIG. 3, when the rim 32 is fully disposed within the trough 104, the outer corners 106 and 108 of the planar rim 32 of the top end 16 of the receptacle sealingly engage the lid at two locations; namely, at the junction of the annular flange with the bottom surface of the body portion of the lid and at the approximate location of the transition of the body portion 42 of the lid into the skirt 60. These two annular sealing locations provide assurance of a complete vacuum and liquid seal between the lid and the receptacle. Notably, the outer edge 108 of the rim 32 of the receptacle engages the inner surface of the trough at a location disposed inwardly of the upper wall 90 of the skirt 60, thereby ensuring that there is sealing of the outer edge 108 to the inner wall of the trough, even in the areas where the ledges and their associated openings are located.

In accordance with another aspect of the present invention, the sealing of the rim of the receptacle in the trough of the lid is enhanced and insured by means of the plurality of ledges disposed about the circumference of the inner surface of the skirt of the lid. Specifically referring to FIG. 7, it may be recognized that the separation distance between the body portion 42 of the lid and the location of each ledge on the inner surface of the skirt of the lid is chosen to be not greater than the distance between the planar rim 32 of the receptacle and the lower edge 28 of the skirt of the receptacle. Further, the width and cross sectional geometry of the trough 104 of the lid is substantially equal to the width and cross sectional geometry of the upper end of the receptacle and its annular skirt so that the rim 32 snugly fits within the trough. Further, the location of the ledge 62 is chosen such that when the receptacle skirt is fully disposed within the trough, the ledge is allowed to move under and engage the lower edge 28 of the rim 32 providing a positive indication that the rim 32 has achieved sealing engagement within the trough and also providing for locking of the lid in engagement with the receptacle. Still further, by reason of the resiliency of the lid skirt 60, once the rim 32 is in place within the trough and the lid skirt is allowed to return toward its relaxed state, there is developed a force system, depicted generally by the arrows "C", "D", "E" and "F", which urges the ledge inwardly and upwardly relative to the receptacle rim 32 and skirt 20 disposed within the trough. This force results in enhancement of the engagement of the side edges of the planar rim with the trough wall, hence enhancement of the sealing of the rim to the lid.

Insertion of the rigid rim 32 of the receptacle into the trough 104 of the lid is made possible by means of the inherent resiliency of the lid skirt 60 and the presence of the ramps 62 associated with each ledge. In the course of fitting the lid to the top end of the receptacle, pressure is exerted against the lid in a direction toward the receptacle. This pressure forces the lateral expansion of the lid skirt by an amount sufficient to permit the receptacle rim 32 to engage the ramps and move past the ledges to fully enter the trough 104. As noted, once the receptacle rim is fully within the trough, the ledges "snap back" under the resilient force of the skirt to engage the lower edge 28 of the receptacle skirt, thereby interlocking the lid and receptacle. As noted, the ledges 62 are spaced apart from one another circumferentially of the lid skirt, preferably 45 degrees apart about the outer circumference of the lid in the instance of a circular lid. If removal of the lid is attempted by lifting outwardly and upwardly on the lid skirt at any given single location about the circumference of the skirt, only a limited portion of the skirt can be deformed. This limited deformation of the lid skirt is only sufficient to permit disengagement of not more than one ledge at a time from the receptacle rim, leaving the remainder of the ledges engaged and in position to retain the lid on the receptacle. As contrasted to the situation where the ledges define a continuous line of engagement with the receptacle rim and limited lateral deformation of the skirt can result in a type of "peeling" of the lid away from the receptacle, in the present invention, disengagement of one ledge does not permit disengagement of adjacent ledges so that there is no peeling effect possible. Advantageously, the present interlocking of the lid with the receptacle has been found to survive dropping of a fluid-filled canister onto a floor from a height of about four feet without destruction of the seal between the lid and the receptacle. Further, after the canister has been used to collect fluids and is ready for disposal of the fluids, the ports leading into and out of the interior of the canister are closed, usually by caps or plugs, and the canister and its contents may be transported safely to its point of disposal, preferably by incineration.

Whereas the present invention has been described in terms of specific embodiments, those skilled in the art will recognize variations and it is intended to limit the invention only as set forth in the claims appended hereto.

What is claimed:

1. A suction canister for use in the collection of fluids from a medical patient comprising an open top receptacle adapted to receive therein said fluids and including a top rim thereon, said top rim including wall means folded outwardly of said receptacle and at least partially back upon itself to define a rim about said top end of said receptacle and an annular skirt depending from said rim and having an annular bottom edge, a lid adapted to cover and close said open top of said receptacle, said lid including a body portion having a bottom surface, a peripheral portion, a resilient annular skirt depending from said peripheral portion and including an inner surface, and an annular flange depending from said bottom surface of said body portion, said skirt and said flange being spaced apart from one another and defining an annular trough therebetween suitable for the receipt of said top rim of said receptacle in sealing engagement therewith, and including means for connecting said receptacle in fluid communication with a source of fluids sought to be collected from a patient, a plurality of substantially rigid ledge means disposed in spaced apart relationship to one another and projecting radially inwardly of said skirt and into said trough a distance which permits the passage therepast by said top rim of said receptacle upon the radially outward flexing of said skirt and in position to engage said rim and interlock the same with said lid when said rim is disposed within said trough and said skirt is relaxed, the interlock being of a nature wherein removal of said lid from said receptacle is prevented other than by substantially destructive force applied to the lid and/or receptacle, and means defining a through opening in said skirt adjacent each of said ledges and extending away from each of said ledges in a direction toward said peripheral portion of said lid, said through opening being adapted to receive and permit the passage therethrough of a shoulder portion of a mold employed in the fabrication of said lid and against which said ledge is formed.

2. The suction canister of claim 1 and including ramp means associated with each of said ledge means for facilitating entry of said receptacle rim into said trough of said lid.

3. The suction canister of claim 1 wherein each of said receptacle and said lid is formed of a moldable plastic.

4. The suction canister of claim 3 wherein said receptacle is formed of a first moldable plastic and said lid is formed of a second moldable plastic, said first moldable plastic being substantially rigid when removed from a mold and said second moldable plastic, when removed from a mold, being deformable to the extent only that said lid skirt is sufficiently deformable to permit the passage of said receptacle rim past said ledge means in the course of insertion of said receptacle rim into said trough in said lid.

5. A suction canister for use in the collection of fluids from a medical patient comprising:

a receptacle including means for connecting said receptacle in fluid communication with a source of fluids sought to be collected from the patient,
    said receptacle including a closed bottom end, an open top end, and wall means joining said bottom and top ends,
    said wall means being folded outwardly of said receptacle and partially back upon itself to define a rim about said top end of said receptacle and an annular skirt depending from said rim and having an annular bottom edge,
    said rim including a substantially planar outer surface having first and second outer side edges,
a lid adapted to cover and close the top end of said receptacle, said lid including
    a body portion having a top surface and a bottom surface and including a peripheral edge,
    an annular skirt depending from said peripheral edge of said body portion and having an inner surface facing inwardly of said lid
    an annular flange depending from the bottom surface of said body portion, said flange being disposed inwardly of said peripherial edge of said body portion, said body portion, said flange and said skirt defining a trough therebetween for the receipt of said rim of said receptacle therein in sealing engagement with said trough,
    a plurality of ledges disposed in spaced apart relationship to one another about the inner circumference of said skirt and projecting laterally inwardly therefrom to define a surface thereof for lockingly engaging said receptacle rim when said rim is in sealing engagement with said trough,
    means defining at least one ramp associated with each of said ledges for facilitating the insertion of said receptacle rim into said trough, and
    means defining a through opening in said skirt adjacent each of said ledges, each opening being adapted to permit the passage therethrough of a shoulder portion of a mold employed in the fabrication of said lid.

* * * * *